United States Patent
Turner

(10) Patent No.: US 9,056,021 B2
(45) Date of Patent: Jun. 16, 2015

(54) SEPARATION DEVICE

(75) Inventor: Nicholas Turner, Devizes (GB)

(73) Assignee: SMITH & NEPHEW PLC (GB)

( * ) Notice: Subject to any disclaimer, the term of this patent is extended or adjusted under 35 U.S.C. 154(b) by 1533 days.

(21) Appl. No.: 12/307,419

(22) PCT Filed: Jul. 4, 2007

(86) PCT No.: PCT/GB2007/002489
§ 371 (c)(1),
(2), (4) Date: Mar. 2, 2009

(87) PCT Pub. No.: WO2008/003957
PCT Pub. Date: Jan. 10, 2008

(65) Prior Publication Data
US 2009/0281547 A1 Nov. 12, 2009

(30) Foreign Application Priority Data

Jul. 5, 2006 (GB) .................................. 0613359.9

(51) Int. Cl.
*A61B 17/58* (2006.01)
*A61F 2/46* (2006.01)
*A61F 2/36* (2006.01)
*A61F 2/40* (2006.01)
*A61F 2/30* (2006.01)

(52) U.S. Cl.
CPC ............ *A61F 2/4637* (2013.01); *A61F 2/3609* (2013.01); *A61F 2/4014* (2013.01); *A61F 2002/30332* (2013.01); *A61F 2002/30738* (2013.01); *A61F 2002/4623* (2013.01); *A61F 2002/4641* (2013.01); *A61F 2220/0033* (2013.01)

(58) Field of Classification Search
USPC ............ 606/22.18, 80–81, 91, 99; 623/22.12, 623/22.18, 22.21, 22.24–22.3, 22.29, 22.43
See application file for complete search history.

(56) References Cited

U.S. PATENT DOCUMENTS

| 4,787,907 | A |   | 11/1988 | Carginan |   |
|---|---|---|---|---|---|
| 5,116,339 | A | * | 5/1992 | Glock | 606/91 |
| 5,362,311 | A |   | 11/1994 | Amino et al. |   |
| 6,132,469 | A | * | 10/2000 | Schroeder | 623/22.24 |
| 7,024,972 | B2 | * | 4/2006 | Werner et al. | 81/443 |
| 2007/0005144 | A1 | * | 1/2007 | Leisinger et al. | 623/22.29 |

FOREIGN PATENT DOCUMENTS

| DE | 19833791 | 1/2000 |
| DE | 20114835 | 12/2001 |
| WO | WO0004885 | 2/2000 |

OTHER PUBLICATIONS

Office Action dated Oct. 12, 2010 in related Chinese Patent Application No. 200780025524.4.
International Search Report in Application No. PCT/GB2007/002489 dated Dec. 6, 2007.
Australian Office Action dated Apr. 2, 2012 in Application No. 2007270930.

* cited by examiner

*Primary Examiner* — Thomas J Sweet
*Assistant Examiner* — Tiffany Shipmon
(74) *Attorney, Agent, or Firm* — Kilpatrick Townsend & Stockton LLP

(57) ABSTRACT

A device (1, 7) for separating a sleeve from an implant head, comprising a drive shaft (2) having a proximal end (3) and a distal end (4), the distal end having a cam (6), wherein the cam is disposed such that when, in use, a torque is applied to the drive shaft via the proximal end the cam acts in a direction substantially parallel to the axis of the drive shaft. A method of separating a sleeve from an implant head using such a device.

19 Claims, 7 Drawing Sheets

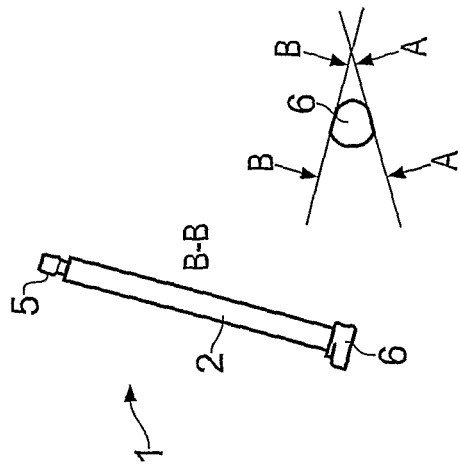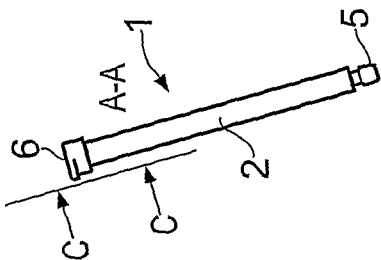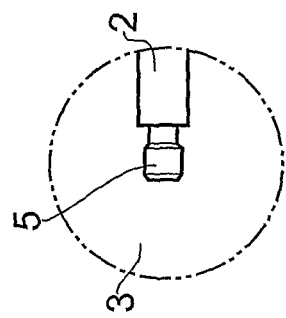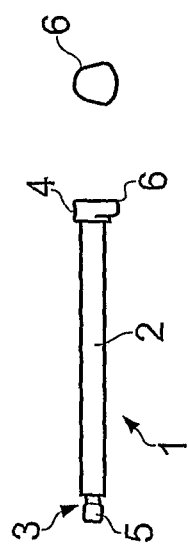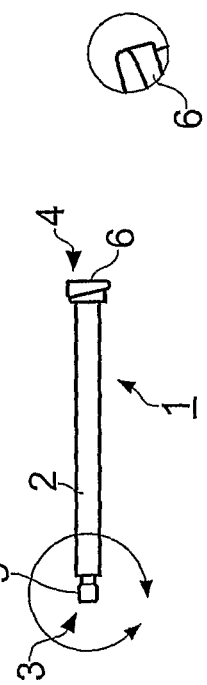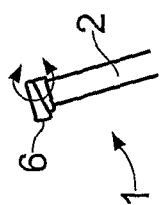

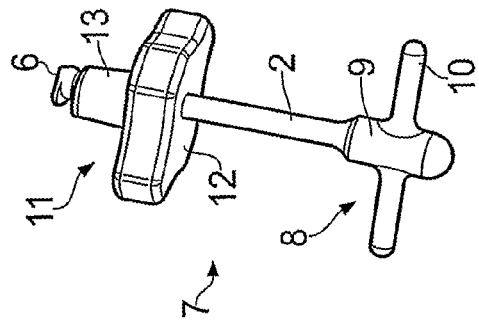
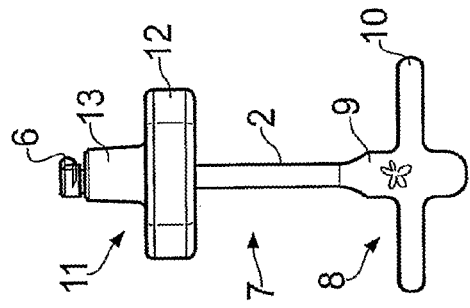
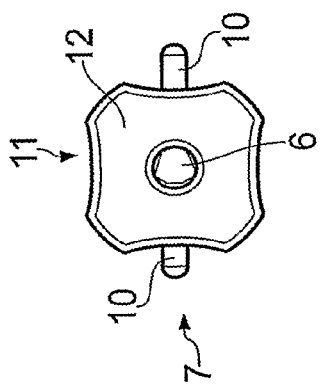
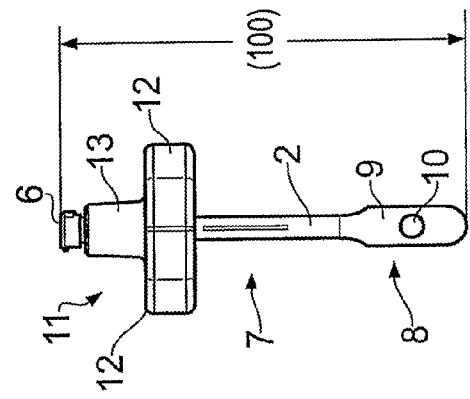
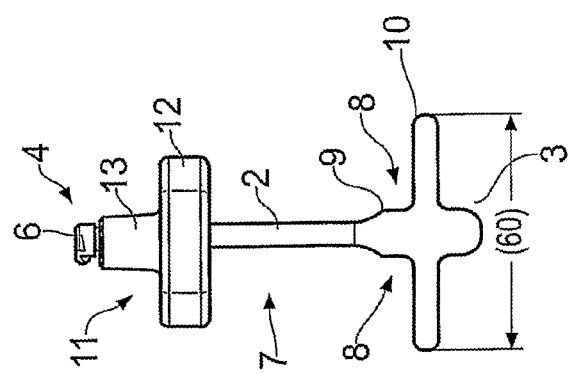

SEPARATION DEVICE

CROSS REFERENCE TO RELATED APPLICATIONS

This application is the U.S. national phase of International Application No. PCT/GB2007/002489 filed on Jul. 4, 2007 and published in English on Jan. 10, 2008 as International Publication No. WO 2008/003957 A2, which application claims priority to Great Britain Application No. 0613359.9 filed on Jul. 5, 2006, the entire contents of both of which are incorporated herein by reference.

FIELD OF THE INVENTION

The present invention relates to a separation device, and particularly a device for separating a sleeve from an implant head.

BACKGROUND OF THE INVENTION

If an incorrect selection (either the head or sleeve) is made the sleeve can become stuck within an implant head, such as a hip implant head. In such circumstances, manual force applied directly by a user, i.e. without the aid of a device/tool, can be insufficient to remove the sleeve. Accordingly, a suitable device is required.

Existing taper sleeves have an internal screw thread at the base of the taper. To remove such taper sleeves, a device with a threaded spigot is used to thread through the bottom surface of the taper sleeve and bear against the recessed internal face of the implant head, thereby forcing the sleeve and the implant head apart. Such a device will not work with a sleeve lacking a screw thread.

Such sleeves require there to be sufficient space for a bottom surface at the base of the sleeve. In some cases where space is limited there is not sufficient space and therefore such sleeves cannot be used.

Sleeves having threaded portions are more difficult to manufacture than those without threaded portions.

Sleeves having threaded portions are prone to failure due to thread burring caused by the threaded spigot separation device.

SUMMARY OF THE INVENTION

An aim of the present invention is to provide a device that can efficiently separate a sleeve from an implant head, regardless of whether the sleeve has a screw thread or not, without causing any damage to the sleeve.

There is provided a device for separating a sleeve from an implant head, comprising a drive shaft having a proximal end and a distal end, the distal end having a cam, wherein the cam is disposed such that when, in use, a torque is applied to the drive shaft via the proximal end the cam acts in a direction substantially parallel to the axis of the drive shaft.

The device can remove both threaded and non-threaded sleeves from an implant head. The device is simple to use and requires minimal force in order to effect separation of the sleeve and implant head. The device does not damage the sleeve. The device enables a surgeon to use non-threaded sleeves, which are easier to manufacture than threaded sleeves, less prone to damage than threaded sleeves (when removed by a threaded spigot separation device), and which can be utilised where space is limited and closed tapers are not possible.

The drive shaft may have a length in the range 40-80 mm. The drive shaft may have a length in the range 50-70 mm. The drive shaft may have a length in the range 55-65 mm.

The drive shaft may have a diameter in the range 4-8 mm. The drive shaft may have a diameter in the range 5-7 mm.

The cam may have an angle in the range 10-14° measured relative to the plane that is perpendicular to the axis of the drive shaft. The cam may have an angle in the range 11-13°. The cam may have an angle of approximately 12°.

The cam is sized so that the leading edges are smaller than the gap size of the cavity space. The cam is sized so that as the cam is rotated the cam increases to greater than the gap size. The cam may be sized so that as the cam is rotated through 180° the cam increases to greater than the gap size. The cam may be sized so that as the cam is rotated through 180° the cam increases to 1.1-2 times the gap size. The cam may be sized so that as the cam is rotated through 180° the cam increases to 1.5 times the gap size.

The proximal end of the device may have a handle, such that, in use, a torque is applied to the drive shaft via the handle.

The handle may comprise a bar disposed perpendicular to the proximal end of the drive shaft. The bar may be disposed such that the bar and the drive shaft form an L-shape. The bar may be disposed such that the bar and the drive shaft form a T-shape.

According to a preferred embodiment of the present invention, the device further comprises a body for engaging with the sleeve, the body having a bore for receiving the drive shaft.

The diameter of the bore may be greater than the diameter of the drive shaft, thereby enabling translation of the cam in a plane substantially perpendicular to the axis defined by the bore.

The bore may have a diameter in the range 4-12 mm. The bore may have a diameter in the range 4-10 mm. The bore may have a diameter in the range 4-8 mm. The bore may have a diameter in the range 5-7 mm.

The axis of the bore may be offset from the main axis of the body so that rotation of the drive shaft results in eccentric motion of the cam with respect to the body.

The body may be tapered so that it can engage with a tapered sleeve.

The body and the drive shaft may have guide marks such that when the guide marks on the body and the drive shaft are aligned, this indicates to a user that the cam is optimally oriented with respect to the body in order to enable insertion into the sleeve.

The body may have a first portion and a second portion, the first and second portions being cylindrical, the first portion having a greater diameter than the second portion, the first and second portions being aligned such that their centre-points are coaxial and the body is substantially T-shaped when viewed in cross-section. The bore extends through both the first and second portions.

The first portion may have a diameter in the range 25-75 mm. The first portion may have a diameter in the range 35-65 mm. The first portion may have a diameter in the range 45-55 mm.

The second portion may have a diameter in the range 10-20 mm. The second portion may have a diameter in the range 10-15 mm. The second portion may have a diameter in the range 11-13 mm.

The combined length of the first and second portions measured along the bore axis may be in the range 20-50 mm. The combined length may be 20-40 mm. The combined length may be 20-30 mm. The combined length may be 25-30 mm.

The first portion of the body may be shaped so that it can be gripped by a user. For example, the first portion may be based on a cylinder with parts of the periphery removed in order to provide indentations that can act as gripping points. The first portion may have at least two gripping points. The first portion may have two opposing gripping points. The first portion may have three gripping points disposed equidistantly around its periphery. The first portion may have four gripping points disposed equidistantly around its periphery.

The second portion of the body may be tapered so that it can engage with a tapered sleeve.

The drive shaft/cam may be made of plastic. Preferably, the drive shaft/cam is made of metal. The metal may be aluminium, titanium, stainless steel or a metal alloy. Preferably, the metal is stainless steel.

The handle may be made of plastic. Preferably, the handle is made of metal. The metal may be aluminium, titanium, stainless steel or a metal alloy. Preferably, the metal is stainless steel.

The body may be made of metal. The metal may be aluminium, titanium, stainless steel or a metal alloy. Preferably, the body is made of plastic. Preferably, the plastic is polyacetal.

There is also provided a method of separating a sleeve from an implant head. The distal end of an embodiment of the device (i.e., the end with the cam) is inserted into a cavity space between the leading face of a sleeve and the internal face of an implant head so that the cam engages with the leading face of the sleeve and the internal face of the implant head. Torque is applied to the drive shaft via the proximal end so that the cam rotates and thereby forces the sleeve and the implant head apart.

Preferably, the proximal end of the device has a handle and torque is applied to the drive shaft via the handle.

The handle may comprise a bar disposed perpendicular to the proximal end of the drive shaft. The bar may be disposed such that the bar and the drive shaft form an L-shape. The bar may be disposed such that the bar and the drive shaft form a T-shape.

According to a preferred embodiment of the present invention, the device further comprises a body for engaging with the sleeve, the body having a bore for receiving the drive shaft, and wherein the body is disposed so that it engages with the sleeve.

The diameter of the bore may be greater than the diameter of the drive shaft, thereby enabling translation of the cam in a plane substantially perpendicular to the axis defined by the bore, so that when the cam is moved within the cavity space it engages with the leading face of the sleeve and the internal face of the implant head.

The axis of the bore may be offset from the main axis of the body so that rotation of the drive shaft results in eccentric motion of the cam with respect to the body, thereby enabling the cam to move from a first position within the confines of the body to a second position outside the confines of the body, such that when the cam is in the second position it is disposed in the cavity space so that it engages with the leading face of the sleeve and the internal face of the implant head.

The sleeve may be tapered. The sleeve may have two tapers, one internal to engage with the male taper of a hip stem, for example, and one external to engage with the internal taper of the implant head.

The body of the device may be tapered so that it can engage with a tapered sleeve.

The drive shaft/cam may be made of plastic. Preferably, the drive shaft/cam is made of metal. The metal may be aluminium, titanium, stainless steel or a metal alloy. Preferably, the metal is stainless steel.

The handle may be made of plastic. Preferably, the handle is made of metal. The metal may be aluminium, titanium, stainless steel or a metal alloy. Preferably, the metal is stainless steel.

The body may be made of metal. The metal may be aluminium, titanium, stainless steel or a metal alloy. Preferably, the body is made of plastic. Preferably, the plastic is polyacetal.

The implant head may be part of a hip implant.

There is further provided a kit of parts comprising a device according to embodiments of the present invention and at least one sleeve, the body of the device and the at least one sleeve being shaped so that they engage one another.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

Reference will now be made, by way of example, to the accompanying drawings, in which:

FIGS. 1a-h show various views of a device according to an embodiment of the present invention;

FIGS. 2a-e show various views of a device according to another embodiment of the present invention;

DETAILED DESCRIPTION OF EMBODIMENTS OF THE INVENTION

Figure 3B:
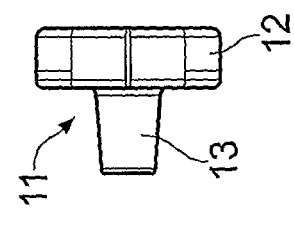
FIGS. 3a-d show various views of a component of the device shown in FIGS. 2a-e.
Figure 3A:
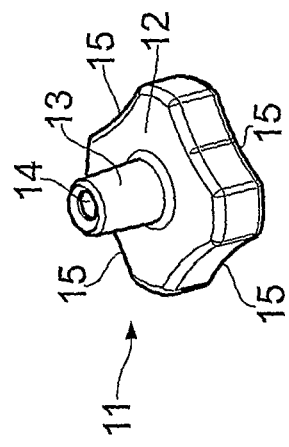
Figure 3C:
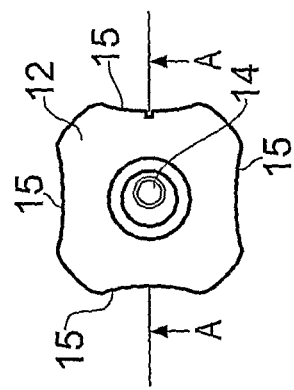

FIGS. 1a to 1h show a device (1) according to an embodiment of the present invention. The device (1) comprises a drive shaft (2) having a proximal end (3) and a distal end (4). The proximal end (3) has a protuberance (5) that can be gripped by any suitable means (for example a user's fingers or pliers) in order to apply a torque to the drive shaft (2). The distal end (4) of the drive shaft (2) has a cam (6). The cam (6) is disposed such that when a torque is applied to the drive shaft (2) via the proximal end (3) the cam (6) acts in a direction substantially parallel to the axis of the drive shaft (2).

FIGS. 1a and 1b are side views of the device (1). FIG. 1c is a bottom plan view, showing the cam (6). FIGS. 1d-g show the cam (6) in more detail. FIG. 1h shows the protuberance (5) in more detail.

A user can insert the distal end (4) into a cavity space between the leading face of a sleeve and the internal face of an implant head (see FIG. 6) so that the cam (6) engages with the leading face of the sleeve and the internal face of the implant head. The user can then apply a torque to the drive shaft (2) via the protuberance (5) on the proximal end (3) of the drive shaft (2) so that the cam (6) rotates and thereby forces the sleeve and implant head apart. The user may apply a torque with his fingers if possible, or with pliers if more force is required. The protuberance (5) may provide an attachment point for a handle, as described herein.

FIGS. 2a-e show a device (7) according to another embodiment of the present invention. The figures show possible dimensions of the device (7) by way of example only, they are not limiting. The device (7) comprises a drive shaft (2) having a proximal end (3) and a distal end (4). The proximal end (3) has a handle (8) which comprises a body (9) and a cross bar (10). The handle (8) is attached to the protuberance (5) of FIGS. 1a-h. The handle enables a user to apply a torque to the proximal end (3) of the drive shaft (2). The distal end (4) of the drive shaft (2) has a cam (6). The cam (6) is disposed such that when a torque is applied to the drive shaft (2) via the handle (8), the cam (6) acts in a direction substantially parallel to the axis of the drive shaft (2).

The device (7) also has a body (11) which comprises a first portion (12) and a second portion (13). The body (11) is shown in more detail in FIGS. 3a-d. The diameter of the first portion (12) is greater than the diameter of the second portion (13). The first (12) and second (13) portions are aligned such that their centre-points are coaxial and the body is substantially T-shaped when viewed in cross-section (see FIGS. 2a-c, 3b). The first portion (12) has four gripping points (15) disposed equidistantly around the periphery of the first portion (12). The second portion (13) is tapered so that it can engage with a tapered sleeve.

Figure 3D:
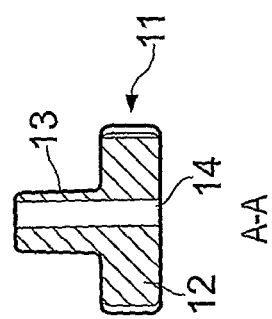
Figure 4A:
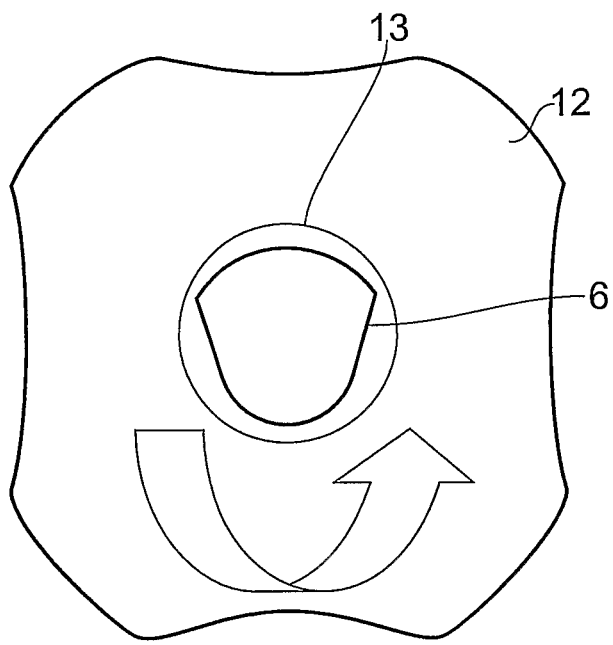
FIGS. 4a,b show bottom plan views of the device of FIGS. 2a-e.
Figure 4B:
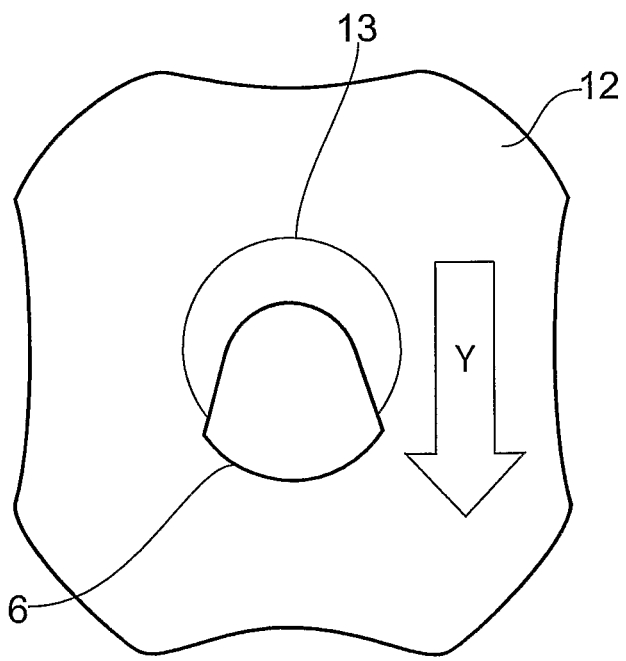
Figure 5:
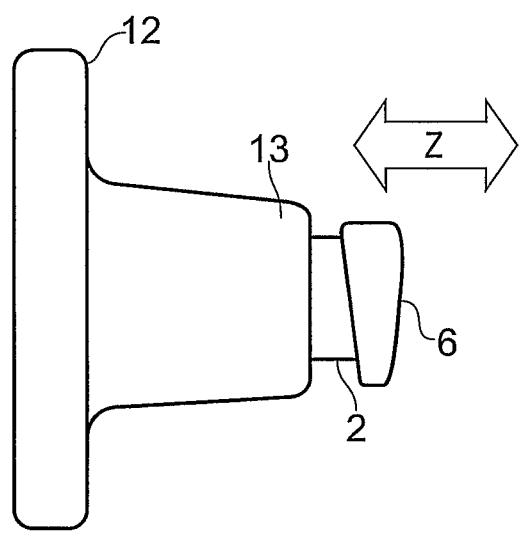
FIG. 5 shows a side view of the device of FIGS. 2a-e.

As shown in FIG. 3d, a bore (14) extends through both the first (12) and second (13) portions. From FIGS. 2a,c and 3a,c,d it can be seen that the central axis of the bore (14) is offset from the main axis of the body (11) so that rotation of the drive shaft (2) results in eccentric motion of the cam (6) with respect to the body (11). This is illustrated in FIGS. 4a,b. As shown in FIGS. 4a,b, rotation of the drive shaft (in this embodiment in a clockwise direction) causes the cam (6) to move out from within the confines of the second portion (13) of the body (11) in direction Y. As shown in FIG. 5, the drive shaft (2) and cam (6) can translate in the direction Z, parallel to the axis of the drive shaft (2).

Figure 6:
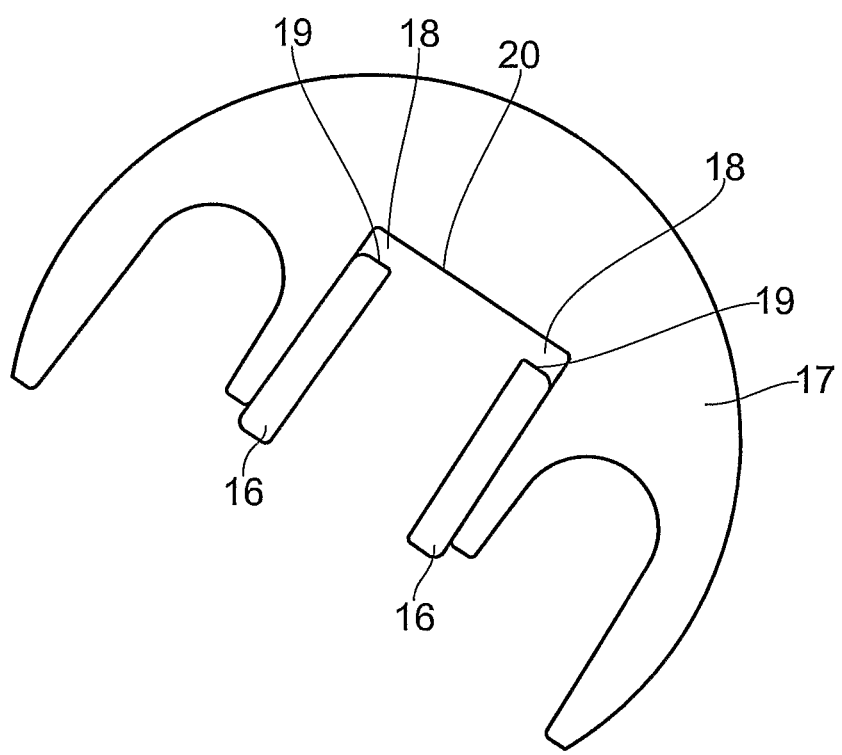
FIG. 6 shows a cross-section of an implant head with a sleeve inserted.

FIG. 6 shows a cross-section of an implant head (17) with a sleeve (16) inserted. As shown, there is a cavity space (18) between the leading face (19) of the sleeve (16) and the internal face (20) of the implant head (17). It is the cavity space (18) that receives the cam (6). The gap size of the cavity space (18) may be 1 mm or more. The gap size of the cavity space (18) may be 2-10 mm. Usually, the gap size of the cavity space is approximately 2 mm.

Figure 7A:
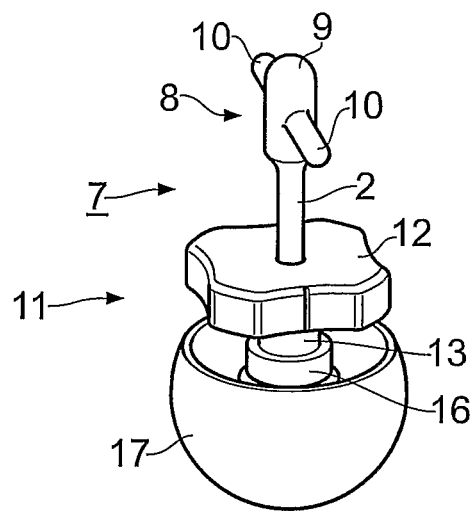
FIGS. 7a-c show various views of the device of FIGS. 2a-e in use with an implant head and sleeve.
Figure 7B:
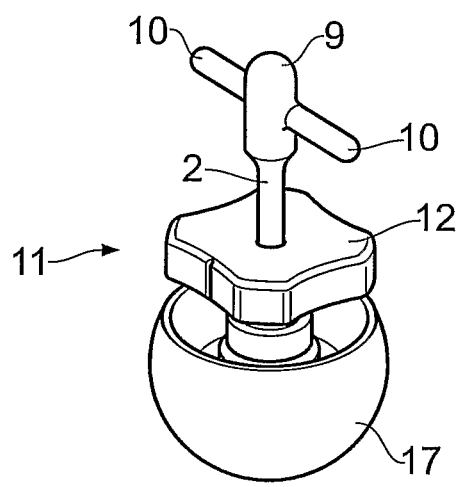
Figure 7C:
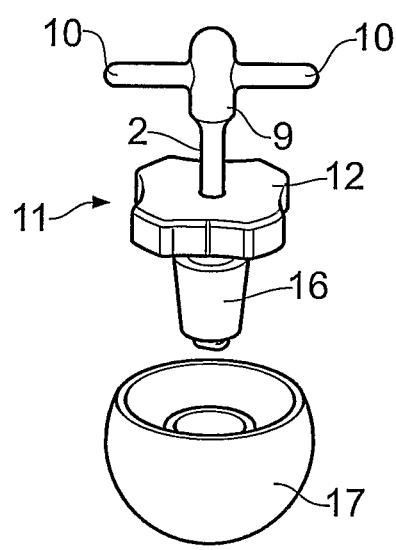

FIGS. 7a-c show the device (7) of FIGS. 2a-e in use with an implant head (17). The distal end (4) of the device (7) is passed into the implant assembly through the rear of the sleeve (16) and allowed to advance until the distal end (4) is inserted into the cavity space (18) between the leading face (19) of the sleeve and the internal face (20) of the implant head (17) (see FIG. 7a and FIG. 6). The second portion (13) of the body (11) locates in the sleeve (16) and thereby centralises the body (11) in the sleeve (16).

As shown in FIG. 7b, a torque is applied to the handle (8) so that the drive shaft (2) rotates. From FIGS. 4a,b it can be seen that such rotation of the drive shaft (2) causes the cam (6) to move out from within the confines of the second portion (13) of the body (11) in direction Y. Consequently, the cam (6) moves in the cavity space (18) and the leading edges of the cam (6) engage with the leading face (19) of the sleeve (16) and the internal face (20) of the implant head (17) (see FIG. 6). As the rotation of the drive shaft (2) and cam (6) continues the cam (6) acts in a direction substantially parallel to the axis of the drive shaft (2) (direction Z in FIG. 5) such that it forces the sleeve (16) and implant head (17) apart (see FIG. 7c).

The drive shaft (2)/cam (6) may be made of plastic. Preferably, the drive shaft (2)/cam (6) is made of metal. The metal may be aluminium, titanium, stainless steel or a metal alloy. Preferably, the metal is stainless steel.

The handle (8) may be made of plastic. Preferably, the handle (8) is made of metal. The metal may be aluminium, titanium, stainless steel or a metal alloy. Preferably, the metal is stainless steel.

The body (11) may be made of metal. The metal may be aluminium, titanium, stainless steel or a metal alloy. Preferably, the body (11) is made of plastic. Preferably, the plastic is polyacetal.

The invention claimed is:

1. A device for separating a sleeve from an implant head comprising a drive shaft having a diameter, an axis, a proximal end, and a distal end, wherein the distal end comprises a cam disposed such that when, in use, a torque is applied to the drive shaft via the proximal end the cam acts in a direction substantially parallel to the axis of the drive shaft.

2. The device of claim 1, further comprising a body for engaging with the sleeve, wherein the body comprises an axis and a bore for receiving the drive shaft.

3. The device of claim 2, wherein the bore comprises an axis and a diameter greater than the diameter of the drive shaft thereby enabling translation of the cam in a plane substantially perpendicular to the axis of the bore.

4. The device of claim 2, wherein the axis of the bore is offset from the axis of the body so that rotation of the drive shaft results in eccentric motion of the cam with respect to the body.

5. The device of claim 2, wherein the sleeve is tapered and at least a portion of the body is tapered for engagement with the tapered sleeve.

6. The device of claim 2, wherein the body comprises plastic.

7. The device of claim 1, wherein the proximal end comprises a handle and wherein, in use, a torque is applied to the drive shaft via the handle.

8. The device of claim 7, wherein the handle comprises a bar disposed perpendicular to the proximal end of the drive shaft.

9. The device of claim 8, wherein the bar is disposed such that the bar and the drive shaft form a T-shape.

10. The device of claim 7, wherein the handle comprises metal.

11. The device of claim 1, wherein the drive shaft and the cam comprise metal.

12. A device for separating a sleeve from an implant head comprising a drive shaft having a diameter, an axis, a proximal end, and a distal end, wherein the distal end comprises a cam disposed on the drive shaft and configured such that when, in use, a torque is applied to the drive shaft via the proximal end, the cam exerts a force on at least one of the sleeve and implant head in a direction substantially parallel to the axis of the drive shaft.

13. The device of claim 12, further comprising a body for engaging with the sleeve, wherein the body comprises an axis and a bore for receiving the drive shaft.

14. The device of claim 13, wherein the bore comprises an axis and a diameter greater than the diameter of the drive shaft thereby enabling translation of the cam in a plane substantially perpendicular to the axis of the bore.

15. The device of claim 14, wherein the axis of the bore is offset from the axis of the body so that rotation of the drive shaft results in eccentric motion of the cam with respect to the body.

16. A device for separating a sleeve from an implant head comprising a drive shaft having a diameter, an axis, a proximal end, and a distal end, wherein a cam is associated with the distal end of the drive shaft such that rotation of the drive shaft rotates the cam, wherein the cam is configured to cause a disconnection force between the sleeve and implant head in a direction substantially parallel to the axis of the drive shaft as the cam rotates.

17. The device of claim 16, further comprising a body for engaging with the sleeve, wherein the body comprises an axis and a bore for receiving the drive shaft.

18. The device of claim 17, wherein the bore comprises an axis and a diameter greater than the diameter of the drive shaft thereby enabling translation of the cam in a plane substantially perpendicular to the axis of the bore.

19. The device of claim 18, wherein the axis of the bore is offset from the axis of the body so that rotation of the drive shaft results in eccentric motion of the cam with respect to the body.

\* \* \* \* \*